US012680887B2

(12) United States Patent
Kim et al.

(10) Patent No.: US 12,680,887 B2
(45) Date of Patent: Jul. 14, 2026

(54) ELECTRONIC DEVICE AND METHOD OF ESTIMATING RATE OF CORE BODY TEMPERATURE CHANGE USING THE SAME

(71) Applicant: SAMSUNG ELECTRONICS CO., LTD., Suwon-si (KR)

(72) Inventors: Sungho Kim, Suwon-si (KR); Sang Kyu Kim, Suwon-si (KR); So Young Lee, Suwon-si (KR); Bok Soon Kwon, Suwon-si (KR); Ho Taik Lee, Suwon-si (KR); Hong Soon Rhee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 506 days.

(21) Appl. No.: 18/122,926

(22) Filed: Mar. 17, 2023

(65) Prior Publication Data

US 2024/0167894 A1     May 23, 2024

(30) Foreign Application Priority Data

Nov. 17, 2022     (KR) ......................... 10-2022-0154711

(51) Int. Cl.
*G01K 13/20*          (2021.01)
*A61B 5/024*          (2006.01)

(52) U.S. Cl.
CPC .......... *G01K 13/20* (2021.01); *A61B 5/02438* (2013.01)

(58) Field of Classification Search
CPC .......... G01K 7/427; G01K 13/20; G01K 3/10; A61B 5/01; A61B 5/02438; A61B 5/681;
(Continued)

(56) References Cited

U.S. PATENT DOCUMENTS 11,406,326 B2     8/2022   Haber et al.
2007/0239038 A1 *  10/2007  Nicolaescu .............. A61B 5/01
                                                   600/549
(Continued)

FOREIGN PATENT DOCUMENTS

CN          112450889 A        3/2021
CN          112656384 A        4/2021
(Continued)

OTHER PUBLICATIONS

Nina Verdel et al., "Reliability and Validity of the Core Sensor to Assess Core Body Temperature during Cycling Exercise", Sensors, Sep. 3, 2021, vol. 21, No. 5932, 13 pages, https://doi.org/10.3390/s21175932.

(Continued)

*Primary Examiner* — Peter J Macchiarolo
*Assistant Examiner* — Mireille S Sadate-Moualeu
(74) *Attorney, Agent, or Firm* — Sughrue Mion, PLLC

(57) ABSTRACT

An electronic device may include: a first sensor configured to measure a skin temperature of skin of a user; a second sensor configured to measure heat flux transmitted from the skin to a main body of the electronic device; a third sensor configured to measure a heart rate of the user; and a processor configured to estimate a rate of core body temperature change based on the skin temperature measured at a first time and a second time, the heat flux, the heart rate, and the skin temperature.

17 Claims, 13 Drawing Sheets

(58) Field of Classification Search
CPC .................. A61B 5/7275; A61B 5/746; A61B 2562/0271; A61B 2560/0247; A61B 5/02055; A61B 5/4866; A61B 5/6824; G16H 50/30; G16H 40/63
USPC ................................................. 600/301, 549
See application file for complete search history.

(56) References Cited

U.S. PATENT DOCUMENTS

| | | | |
|---|---|---|---|
| 2013/0158368 A1* | 6/2013 | Pacione ................. | A61B 5/318 600/595 |
| 2015/0071325 A1* | 3/2015 | Kuroyama ............. | A61B 5/683 374/134 |
| 2017/0086741 A1* | 3/2017 | Bly ........................ | A61B 5/274 |
| 2020/0037884 A1 | 2/2020 | Ishida et al. | |
| 2020/0359906 A1 | 11/2020 | Tanaka | |
| 2021/0076945 A1 | 3/2021 | Imamura | |
| 2022/0125388 A1 | 4/2022 | Buller et al. | |
| 2022/0354424 A1* | 11/2022 | Kuisma .............. | A61B 5/02055 |

FOREIGN PATENT DOCUMENTS

| | | |
|---|---|---|
| CN | 113188683 B | 1/2022 |
| CN | 114623948 A | 6/2022 |
| JP | 6675552 B2 | 4/2020 |
| KR | 10-2021-0006073 A | 1/2021 |
| KR | 10-2022-0093028 A | 7/2022 |
| WO | 2022/127628 A1 | 6/2022 |

OTHER PUBLICATIONS

Alexander P. Welles et al., "Estimation of core body temperature from skin temperature, heat flux, and heart rate using a Kalman filter", Comput Biol Med., Aug. 1, 2018, 6 pages, doi: 10.1016/j.compbiomed.2018.05.021.
Patrick Eggenberger et al., "Prediction of Core Body Temperature Based on Skin Temperature, Heart Flux, and Heart Rate Under Different Exercise and Clothing Conditions in the Heat in Young Adult Males", Front Physiol., Dec. 10, 2018, 11 pages, doi: 10.3389/fphys.2018.01780.
Extended European Search Report issued Sep. 26, 2023 issued by the European Patent Office for EP Patent Application No. 23171064.1.
Jacques Malchaire et al., "Evaluation of the Metabolic Rate Based on the Recording of the Heart Rate", Ind. Health 2017, 55 (3), pp. 219-232, https://doi.org/10.2486/indhealth.2016-0177.
Yuxiang Sun et al., "Comparison of Wrist Skin Temperature with Mean Skin Temperature Calculated with Hardy and Dubois's Seven-Point Method While Sleeping", Energy Build, 2022, 259, 111894, https://doi.org/10.1016/j.enbuild.2022.111894, (3 pages).

* cited by examiner

1

ELECTRONIC DEVICE AND METHOD OF ESTIMATING RATE OF CORE BODY TEMPERATURE CHANGE USING THE SAME

CROSS-REFERENCE TO RELATED APPLICATION(S)

This application claims priority from Korean Patent Application No. 10-2022-0154711, filed on Nov. 17, 2022, in the Korean Intellectual Property Office, the disclosure of which is incorporated herein by reference in its entirety.

BACKGROUND

Field

Apparatuses and methods consistent with example embodiments relate to estimating a rate of change in core body temperature.

Description of the Related Art

Body temperature is one of the four vital signs that has significant clinical significance. A body temperature sensor may be applied to various applications, such as detecting infections in patients, monitoring thermal side effects of medications, or tracking ovulation time in women, and the like.

Body temperature sensors may be classified into contact type sensors and non-contact type sensors. Examples of the contact type sensor may include a sensor for detecting a change in electrical resistance, such as a Resistance Temperature Detector (RTD), a thermistor, etc., a thermocouple for detecting electromotive force, and the like. Further, examples of the non-contact type sensor may include a thermopile, a micro-bolometer, etc., which measure body temperature by detecting infrared rays radiating from a body surface.

Generally, measuring core body temperature accurately with portable devices like wearable devices is challenging. This is because changes in environment factors, such as external temperature, air flow, humidity, etc., affect heat transfer, resulting in differences between skin temperature and core body temperature.

SUMMARY

According to an aspect of the present disclosure, an electronic device may include: a first sensor configured to measure a skin temperature of skin of a user; a second sensor configured to measure heat flux transmitted from the skin to a main body of the electronic device; a third sensor configured to measure a heart rate of the user; and a processor configured to estimate a rate of core body temperature change based on the skin temperature measured at a first time and a second time, the heat flux, the heart rate, and the skin temperature.

The processor may be further configured to: estimate a rate of skin temperature change based on the skin temperature measured at the first time and the second time; estimate energy metabolism based on the heart rate; and estimate the rate of core body temperature change based on the rate of skin temperature change, the energy metabolism, and the heat flux.

In response to the rate of core body temperature change being greater than or equal to a predetermined threshold value, the processor may be further configured to provide notification information about risk of abnormal body temperature.

The processor may be further configured to generate a trend graph showing the rate of core body temperature change over a predetermined period of time.

The processor is further configured to generate a graphic object at a position corresponding to a time point, at which the rate of core body temperature change is greater than or equal to the threshold value, on the trend graph to provide the user with a warning.

Based on a core body temperature being determined to be abnormal, the processor may be further configured to provide notification information requesting the user to stop an outdoor activity by using a text message or a voice message.

The first time precedes the second time, and the processor may be further configured to estimate a core body temperature at the second time by applying the rate of core body temperature change to the core body temperature measured at the first time.

In response to the estimated core body temperature falling outside a predetermined threshold range, the processor may be further configured to provide notification information about a risk of abnormal body temperature.

The second sensor may be a heat flux sensor configured to measure the heat flux.

The electronic device may further include a temperature sensor spaced apart from the first sensor, and configured to measure an internal temperature inside the main body and measure the heat flux based on the skin temperature and the internal temperature inside the main body.

At least one of the first sensor and the temperature sensor may be a thermistor.

A vertical distance between the contact surface and the first temperature sensor is 5 mm in a thickness direction of the main body.

The third sensor may be at least one of a photoplethysmography (PPG) sensor and an electrocardiography (ECG).

According to another aspect of the present disclosure, a method of estimating a rate of core body temperature change in an electronic device is provided. The method may include: measuring a skin temperature of skin of a user; measuring heat flux transmitted from the skin to a main body of the electronic device; measuring a heart rate of the user; and estimating the rate of core body temperature change based on the skin temperature measured at a first time and a second time, the heat flux, the heart rate, and the skin temperature.

The estimating of the rate of core body temperature change may include: estimating a rate of skin temperature change based on the skin temperature measured at the first time and the second time; estimating energy metabolism based on the heart rate; and estimating the rate of core body temperature change based on the rate of skin temperature change, the energy metabolism, and the heat flux.

The method may further include, in response to the rate of core body temperature change being greater than or equal to a predetermined threshold value, providing the user with notification information about risk of abnormal body temperature through an output interface.

The providing of the notification information about the risk of abnormal body temperature may include generating a trend graph showing the rate of core body temperature change over a predetermined period of time.

The first time precedes the second time, and the method may further include: estimating a core body temperature by applying the rate of core body temperature change to the core body temperature measured at the first time.

According to another aspect of the present disclosure, a wearable device may include: a main body; a strap connected the main body; a skin temperature sensor configured to measure a skin temperature of a user at a first time and a second time; a heat flux sensor configured to measure a heat flux between a skin of the user and the main body; a heart rate sensor configured to measure a heart rate of the user; and a processor configured to estimate a rate of core body temperature change based on the skin temperature measured at the first time and the second time, the heat flux, and the heart rate.

The wearable device may further include a display, wherein in response to the rate of core body temperature change being greater than or equal to a predetermined threshold value, the processor may be further configured to provide notification information about a risk of abnormal body temperature through the display.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
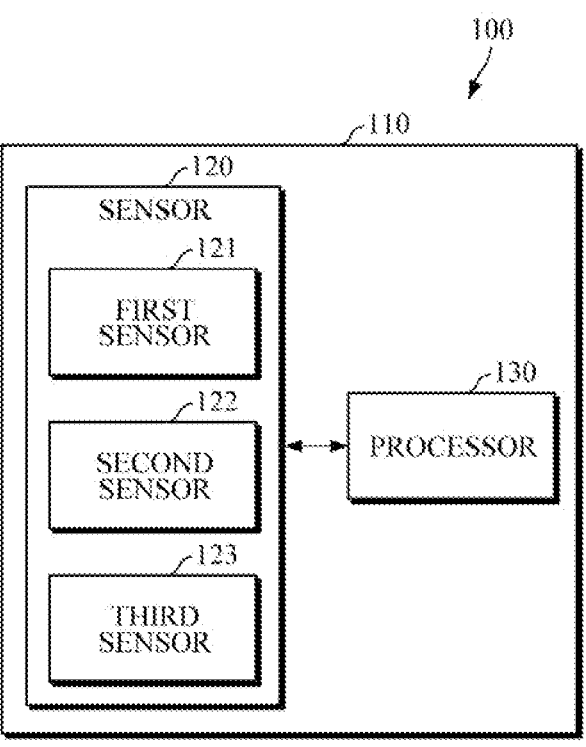
FIG. 1 is a block diagram illustrating an electronic device according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'unit' or 'module', etc., should be understood as a unit that performs at least one function or operation and that may be embodied as hardware, software, or a combination thereof. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

An electronic device according to various embodiments of the present disclosure which will be described below may include, for example, at least one of a wearable device, a smartphone, a tablet PC, a mobile phone, a video phone, an electronic book reader, a desktop computer, a laptop computer, a netbook computer, a workstation, a server, a PDA, a portable multimedia player (PMP), an MP3 player, a medical device, and a camera. The wearable device may include at least one of an accessory type wearable device (e.g., wristwatch, ring, bracelet, anklet, necklace, glasses, contact lens, or head mounted device (HMD)), a textile/clothing type wearable device (e.g., electronic clothing), a body-mounted type wearable device (e.g., skin pad or tattoo), and a body implantable type wearable device. However, the wearable device is not limited thereto and may include, for example, various portable medical measuring devices (antioxidant measuring device, blood glucose monitor, heart rate monitor, blood pressure measuring device, thermometer, etc.), magnetic resonance angiography (MRA), magnetic resonance imaging (MRI), computed tomography (CT), imaging system, ultrasonic system, etc.), and the like. However, the electronic device is not limited to the above devices.

Figure 2A:
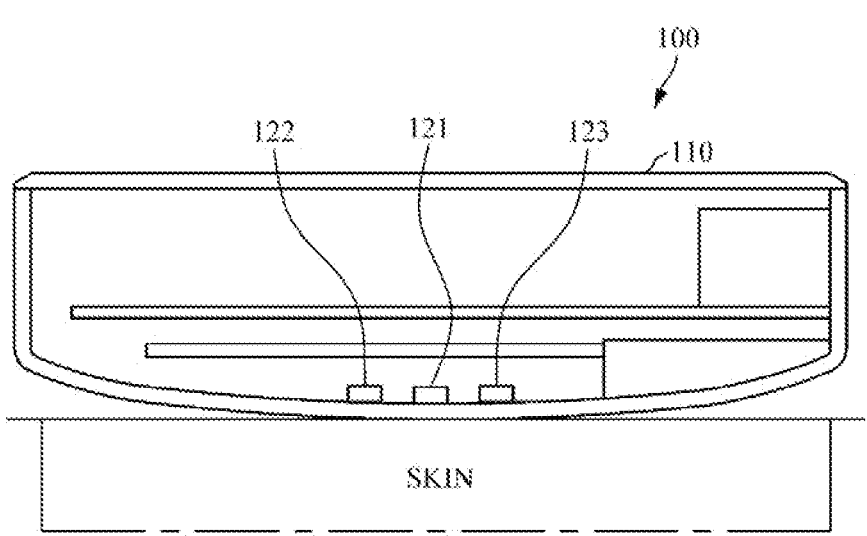
FIGS. 2A and 2B are diagrams illustrating structures of an electronic device according to an embodiment of the present disclosure.
Figure 2B:
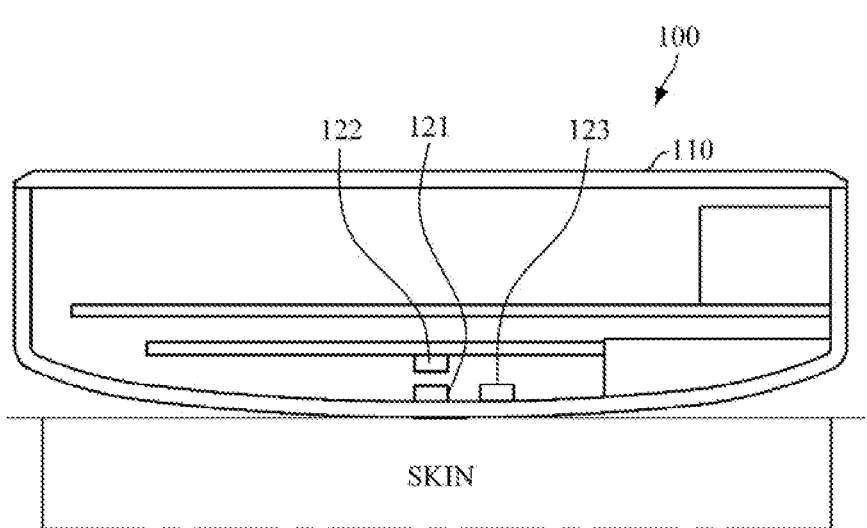

FIG. 1 is a block diagram illustrating an electronic device according to an embodiment of the present disclosure. FIGS. 2A and 2B are diagrams illustrating structures of an electronic device according to an embodiment of the present disclosure.

Referring to FIG. 1, an electronic device 100 includes a sensor 120 and a processor 130 which are mounted in a main body 110. The sensor 120 may include a plurality of sensors and may obtain data for estimating a rate of change in core body temperature. The processor 130 may estimate a rate of change in core body temperature of a user by using the data obtained by the sensor 120.

The sensor 120 may include a first sensor 121 that measures a user's skin temperature, a second sensor 122 that measures heat flux, and a third sensor 123 that measures a user's heart rate. The first sensor 212, the second sensor 122, and the third sensor 123 may be referred to as a temperature sensor, a heat flux sensor, and a heat rate sensor, respectively.

Referring to FIG. 2A, for example, the first sensor 120 may be a temperature sensor capable of measuring temperature of a user's skin at a contact surface of the main body 110 when an object (e.g. user's wrist) comes into contact with the contact surface of the main body 110. To increase the accuracy of the measured skin temperature, the first sensor 121 may be placed at a shortest possible distance from the contact surface of the main body 110. For example, a vertical distance between the contact surface and the first sensor 121 may be less than or equal to 5 mm in a thickness direction of the main body 110. Temperature sensors such as thermistor, thermocouple, silicon temperature sensor, infrared temperature sensor, and the like may be used as the first sensor 121, but the types of temperature sensors are not limited thereto.

The second sensor 122 may be a sensor for measuring heat flux vertically transmitted from the skin to the main body 110, and may be a heat flow sensor that includes a thermopile, a thermocouple, or a resistance thermometer that measures temperature differences across a surface and a heat flux transducer that converts temperature differences into a heat flux value. The heat flux may indicate a rate of heat transfer from the skin to the main body 110. In this case, the heat flux may be measured by vertically mounting another temperature sensor without providing a separate heat flux sensor. For example, referring to FIG. 2B, the second sensor 122 may be a temperature sensor spaced apart from the first sensor 121 that measures the skin temperature and configured to measure temperature inside the main body, and heat flux may also be measured based on a difference between the skin temperature measured by the first sensor 121 and the temperature inside the main body which is measured by the second sensor 122. In this case, thermistor, thermocouple, silicon temperature sensor, and the like may also be used as the second sensor 122.

The third sensor 123 may be a sensor for measuring a user's heart rate, and may be, for example, a Photoplethysmography (PPG) sensor or an electrocardiography (ECG) sensor. In this case, the third sensor 123 may be placed at a position as close to the contact surface as possible to improve the measurement accuracy.

The processor 130 may be electrically connected to the sensor 120 and may control the sensor 120 in response to a request for estimating a rate of core body temperature change.

The processor 130 may estimate a rate of change in core body temperature based on the skin temperature measured by the first sensor 121 at a previous time, the heat flux measured by the second sensor 122 at a previous time, the heart rate measured by the third sensor 123 at a previous time, and skin temperature measured at a current time. In this case, compared to the current measurement time, the previous time may vary according to a setting of an electronic device, and the previous time compared to the current time may be set to, for example, one minute or less.

First, the processor 130 may estimate a rate of skin temperature change based on the skin temperature measured at the previous time and skin temperature measured at the current time. For example, by setting an interval between a current time t2 and a previous time t1 to one minute, the first sensor 121 may continuously measure the first temperature over time, and the processor 130 may estimate the rate of skin temperature change based on the measured values.

Then, the processor 130 may estimate energy metabolism based on the heart rate measured at the previous time.

For example, the processor 130 may obtain the heart rate at the previous time by analyzing cycles of a pulse wave signal (e.g., PPG signal) measured by the third sensor 123. For example, upon obtaining a PPG signal with 100 cycles over one minute, the processor 130 may determine the heart rate to be 100.

The processor 130 may estimate the energy metabolism based on the obtained heart rate. For example, the processor 130 may estimate energy metabolism M by using the obtained heart rate HRwm according to the following Equation 1.

$$M = \frac{(MWC - M_0)}{(HR_{max} - HR_0)}(HR_{wm} - HR_0) + M_0 \qquad \text{[Equation 1]}$$

Herein, $M_0$ denotes resting metabolism, e.g., metabolism at rest or basal metabolism, and is generally 60 W/m$^2$ for adult men. $HR_0$ denotes a resting heart rate, e.g., heart rate at rest. Maximum work capacity in watts (MWC) denotes metabolism at maximum work capacity, and $HR_{max}$ denotes a maximum heart rate. In this case, $M_0$ and $HR_0$ may be values previously measured and stored, and MWC and $HR_{max}$ may be values that can be estimated for each age and gender, and the processor 130 may estimate the values by receiving age and gender input by a user through an interface by using a display device or by using previously stored values.

Then, the processor 130 may measure the heat flux at the previous time. For example, if the second sensor 122 is a temperature sensor disposed in the main body, the processor 130 may measure the heat flux based on a difference between the skin temperature at the previous time and the temperature inside the main body at the previous time. In this case, if the second sensor 122 is a heat flux sensor, the measured heat flux value may be used directly.

Subsequently, the processor 130 may estimate a rate of core body temperature change based on the estimated rate of skin temperature change, the estimated energy metabolism, and the heat flux measured at the previous time, which may be represented by the following Equations 2 and 3.

$$A = (C_{bl} \times V_{bl} + K_{min}) \times (T_{cr} - T_{sk}) \qquad \text{[Equation 2]}$$

$$\frac{\frac{dT_{cr}}{dt}}{\frac{dT_{sk}}{dt}} = \frac{(C_{sk} \times W_{sk})[M - q_{res} - A]}{(C_{cr} \times W_{cr})[A - HF - q_{loss}]} \qquad \text{[Equation 3]}$$

Herein, $$\frac{dT_{cr}}{dt}$$

denotes the rate of core body temperature change, $$\frac{dT_{sk}}{dt}$$

denotes the rate of skin temperature change, $C_{sk}$ denotes a predetermined specific heat of the skin, $C_{cr}$ denotes a predetermined specific heat of the core, $W_{sk}$ denotes a predetermined mass of skin, $W_{cr}$ denotes a predetermined mass of the core, M denotes energy metabolism, HF denotes heat flux, $q_{res}$ denotes a predetermined heat loss resulting from respiration, $q_{loss}$ denotes a predetermined heat loss resulting from skin and perspiration, $C_{bl}$ denotes a predetermined specific heat of blood, $V_{bl}$ denotes a predetermined volume of blood flowing to the skin per unit body surface area, $K_{min}$ denotes a predetermined heat conductivity between the skin and core, $T_{cr}$ denotes a predetermined core body temperature, and $T_{sk}$ denotes the skin temperature measured at the previous time. In this case, normal core body temperature of 36.5° C. may be used as the core body temperature $T_{cr}$ during the initial measurement, or a user's core body temperature measured by an external source may also be used.

Then, if the estimated rate of core body temperature change is greater than or equal to a predetermined threshold value, the processor 120 may generate a notification message through an output interface, alerting the user about the potential risk of abnormal body temperature through an output interface. In this case, if the core body temperature is indeed determined to be abnormal, the processor 130 may send a text message or a voice message requesting the user to discontinue outdoor activities.

Figure 3:
FIG. 3 is a diagram illustrating an example of providing notification information about the risk of abnormal body temperature by a wristwatch-type wearable device.

FIG. 3 is a diagram illustrating an example of providing notification information about the risk of abnormal body temperature by a wristwatch-type wearable device. Referring to FIG. 3, for example, if the estimated rate of core body temperature change is greater than or equal to a predetermined threshold value (e.g., 0.3° C./10 min), the processor 130 may output a text message 320, "WARNING! HIGH BODY TEMPERATURE," and "it is advised to stop outdoor activities and move to cool area," via a display device 310.

In this case, the processor 130 may also output a voice message requesting to stop outdoor activities, or may output the text message and the voice message at the same time. In addition, the processor 130 may also output a warning alarm through the output interface. Upon providing the notification information about the risk of abnormal body temperature, if the estimated rate of core body temperature change remains at a level greater than or equal to the threshold value, the processor 130 may communicate with an electronic device (e.g., smartphone) to directly call the 911 emergency center. The method of providing the notification information about the risk of abnormal body temperature is not limited thereto.

In another embodiment, the processor 130 may generate a trend graph showing a rate of core body temperature change over a predetermined period of time, and may output the graph through the output interface. In this case, in order to provide a user with a warning, the processor 130 may output a predetermined graphic object at a position corresponding to a time point, at which the rate of core body temperature change is greater than or equal to the threshold value, on the graph.

Figure 4:
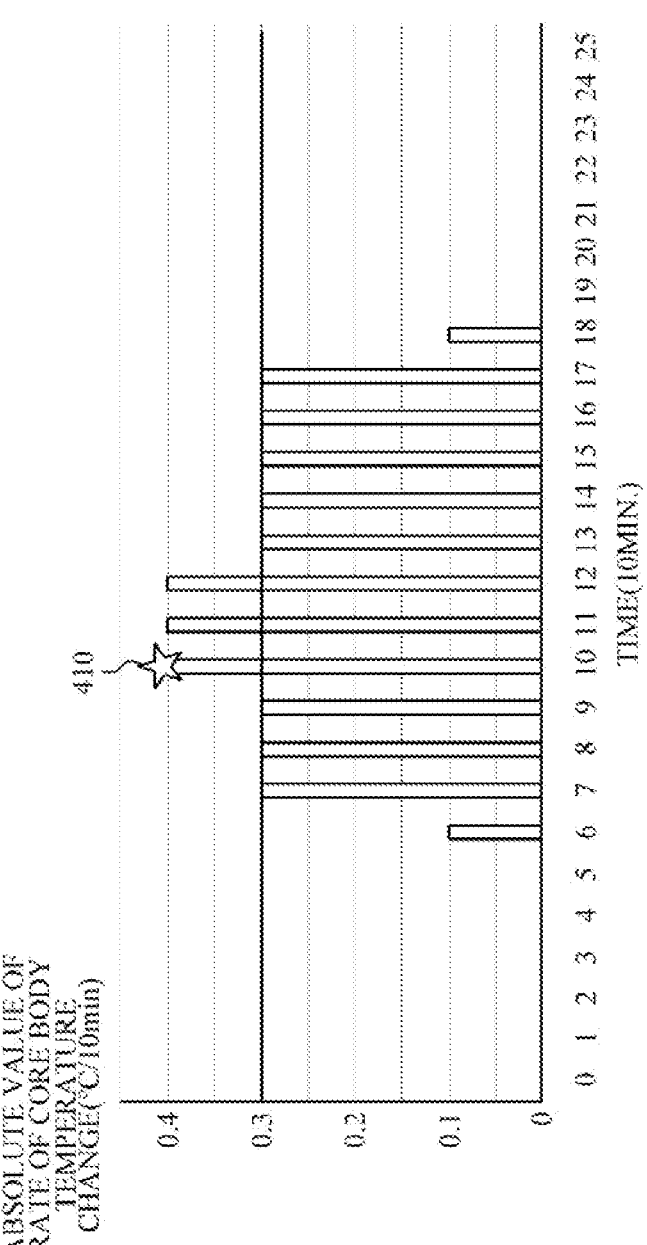
FIG. 4 is a diagram illustrating a trend graph showing a rate of core body temperature change according to an embodiment of the present disclosure.

FIG. 4 is a diagram illustrating a trend graph showing absolute value of a rate of core body temperature change according to an embodiment of the present disclosure. Referring to FIG. 4, it can be seen that a rate of core body temperature change passes 0.3° C./l0 min when 100 minutes elapse after measurement. Assuming that a threshold value is 0.3° C./10 min, the processor 130 may determine that a sudden change in core body temperature occurs 100 minutes after the measurement, and the processor 130 may separately output a star-shaped (☆) graphic object 410 to the display device to provide a user with a warning about the sudden change in the core body temperature.

Warning of a sudden change in core body temperature to the user not only notifies the user of a risk of abnormal body temperature such as fever or hypothermia, but also provides health care services to the user. For example, if a sudden change in core body temperature occurs during exercise, the user may be notified of this, and the user may adjust the exercise intensity. A service provided using the core body temperature change rate is not limited thereto.

Generally, it is difficult to accurately estimate the core body temperature based on only the skin temperature by using a portable device such as a wearable device. However, according to the embodiment of the present disclosure, without directly estimating the core body temperature, the rate of core body temperature change may be estimated by using the rate of skin temperature change which may be easily measured by using a wearable device, and notification information about the risk of abnormal body temperature may be provided rapidly to a user.

The processor 130 may also directly estimate core body temperature by applying core body temperature at a previous time to the estimated rate of core body temperature change. In this case, if the previous time is an initial measurement time, normal core body temperature of 36.5° C. may be used as the core body temperature, or a user's core body temperature measured by an external source may also be used.

Figure 5:
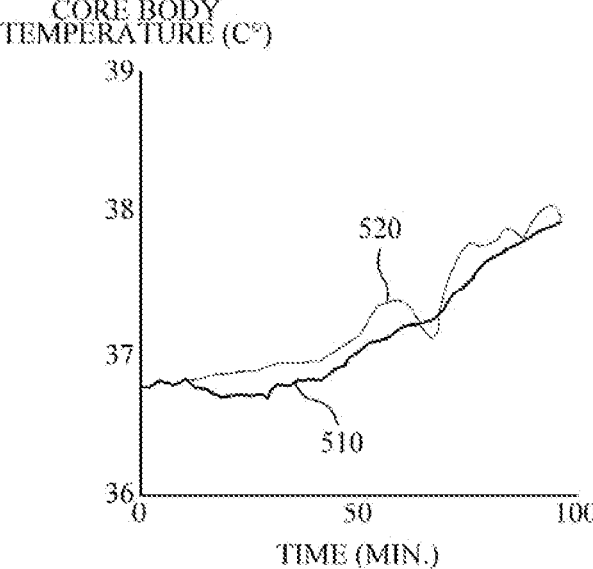
FIG. 5 is a graph illustrating a relationship between an actual core body temperature and core body temperature estimated using a rate of core body temperature change.

FIG. 5 is a graph illustrating a relationship between an actual core body temperature and an estimated core body temperature that is estimated using a rate of core body temperature change. As observed in FIG. 5, the estimated core body temperature 520 fluctuates more than the actual core body temperature 510 over time, while the actual core body temperatures 510 and the actual core body temperature 520 change in a similar trend, and thus are highly correlated.

In this case, if the estimated core body temperature falls outside a predetermined threshold range, the processor 130 may provide a user with notification information about the risk of abnormal body temperature. For example, if the estimated core body temperature falls outside a range of 38° C. to 40° C., the processor 130 determines that the core body temperature is abnormal, and may provide the user with the notification information about the risk of abnormal body temperature. As the method of providing the notification information, a method similar to the above method used in the case where the rate of core body temperature change is greater than or equal to the threshold value (e.g. FIG. 3) may be used, but is not limited thereto.

Figure 6:
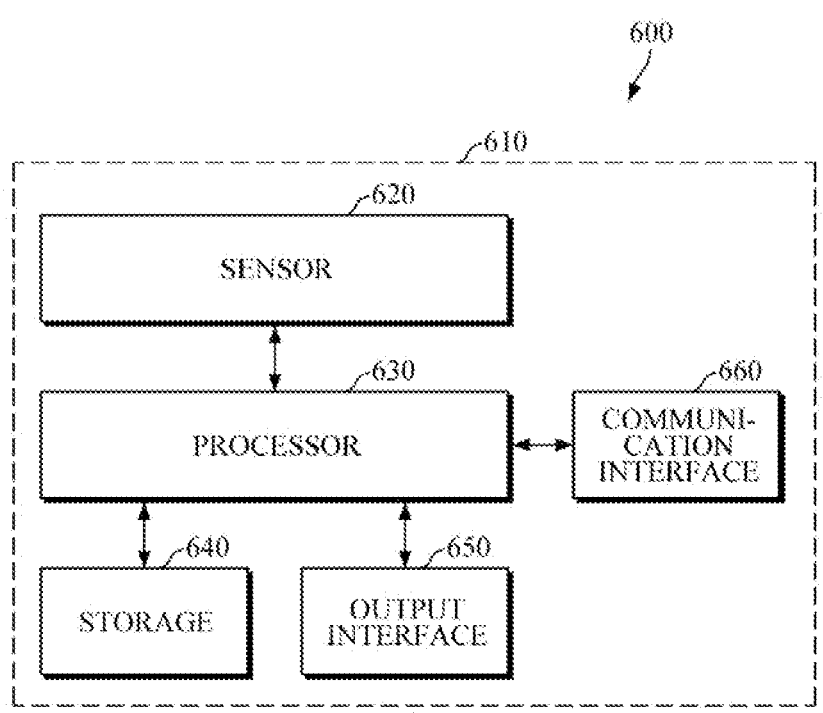
FIG. 6 is a block diagram illustrating an electronic device according to another embodiment of the present disclosure.

FIG. 6 is a block diagram illustrating an electronic device according to another embodiment of the present disclosure.

Referring to FIG. 6, an electronic device 600 includes a sensor 620, a processor 630, a storage 640, an output interface 650, and a communication interface 660 which are mounted in a main body 610. In this case, the sensor 620 and the processor 630 are the same as the sensor 120 and the processor 130 in the embodiment of FIG. 1, such that a detailed description thereof will be omitted.

The storage 640 may store information related to estimating a rate of core body temperature change. For example, the storage 640 may store temperature data, heat flux, and heart rate which are obtained by the sensor 620, processing results of the processor 830, e.g. a rate of skin temperature change, energy metabolism, a rate of core body temperature change, and the like.

The storage 640 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 650 may provide a user with processing results of the processor 630.

For example, the output interface 650 may display a rate of core body temperature change, which is estimated by the processor 630, in a graph and the like on a display, and if the rate of core body temperature change is greater than or equal to a threshold value, the output interface 650 may provide a user with a warning message about abnormal body temperature by using a text message or a voice message in order to provide the user with a warning.

The communication interface 660 may communicate with an external device to transmit and receive various data related to estimating the rate of core body temperature change. The external device may include an information processing device, such as a smartphone, a tablet PC, a desktop computer, a laptop computer, and the like. For example, the communication interface 660 may transmit the estimated rate of core body temperature change to an external device such as a smartphone and the like, and a user may monitor the rate of core body temperature change over time by using, e.g., the smartphone.

The communication interface 660 may communication with the electronic device by using various wired and wireless communication techniques including Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, 5G, and 6G communications, and the like. However, the communication techniques are not limited thereto.

Figure 7:
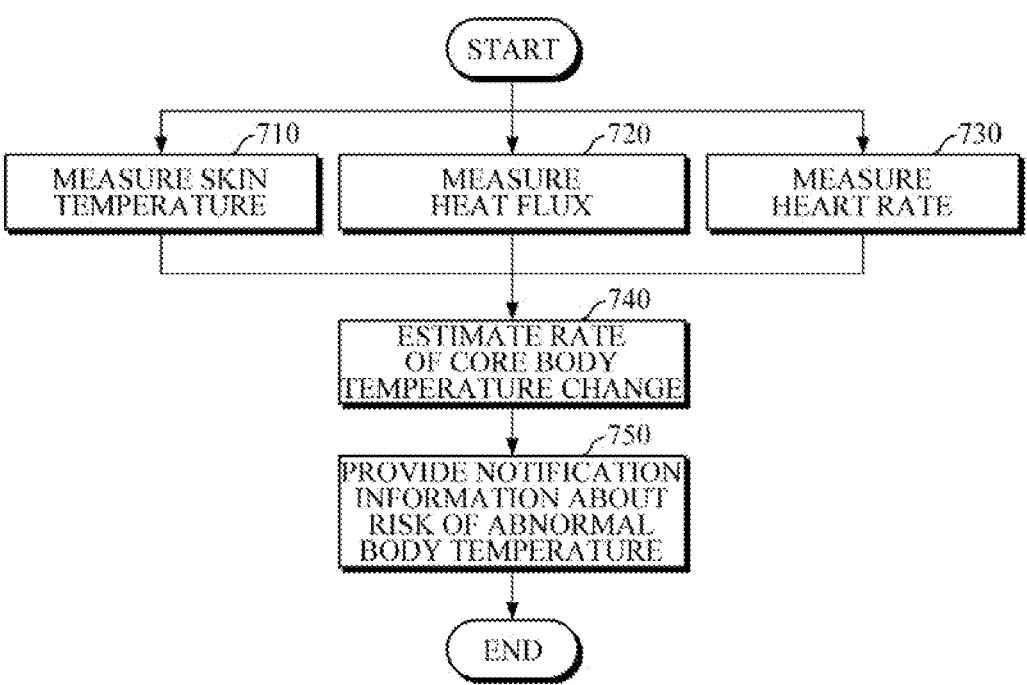
FIGS. 7 and 8 are flowcharts illustrating a method of estimating a rate of core body temperature change according to an embodiment of the present disclosure.
Figure 8:
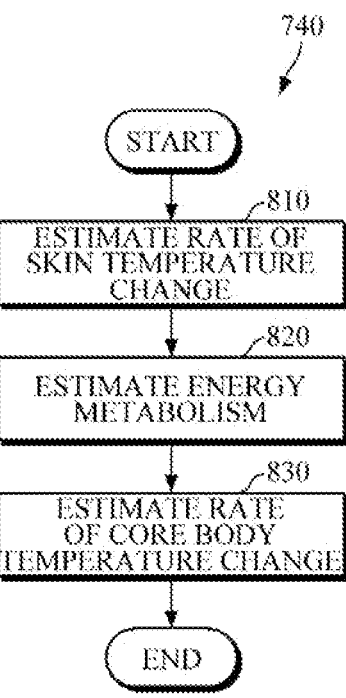

FIGS. 7 and 8 are flowcharts illustrating a method of estimating a rate of core body temperature change according to an embodiment of the present disclosure. FIGS. 7 and 8 are an example of a method of estimating a rate of core body temperature change performed by the electronic devices 100 and 600, which are described in detail above, and thus will be briefly described below in order to avoid redundancy.

Referring to FIG. 7, the electronic device may measure a user's skin temperature by using the first sensor in operation 710, may measure heat flux vertically transmitted from the skin to the main body by using the second sensor in operation 720, and may measure a user's heart rate by using the third sensor in operation 730.

Then, the electronic device may estimate a rate of core body temperature change based on the skin temperature measured by the first sensor at a previous time, the heat flux measured by the second sensor at a previous time, the heart rate measured by the third sensor at a previous time, and skin temperature measured at a current time in operation 740. In this case, compared to the current measurement time, the previous time may vary according to a setting of an electronic device, and the previous time compared to the current time may be set to, for example, one minute or less.

FIG. 8 is a flowchart illustrating in detail the estimating of the rate of core body temperature change in operation 740.

Referring to FIG. 8, the electronic device may estimate a rate of skin temperature change based on the skin temperature measured at the previous time and the skin temperature measured at the current time in operation 810. For example, by setting an interval between the current time t2 and the previous time t1 to one minute, the first sensor may continuously measure the first temperature over time, and the electronic device may estimate the rate of skin temperature change based on the measured values.

Then, the electronic device may estimate energy metabolism based on the heart rate measured at the previous time in operation 820. For example, the electronic device may obtain a heart rate based on a signal obtained by the PPG sensor or the ECG sensor, and may estimate the energy metabolism by using the obtained heart rate according to Equation 1.

Subsequently, the electronic device may estimate a rate of core body temperature change based on the estimated rate of skin temperature change, the estimated energy metabolism, and the heat flux measured at the previous time according to Equations 2 and 3 in operation 830.

Next, if the estimated rate of core body temperature change is greater than or equal to a predetermined threshold value, the electronic device may provide a user with notification information about the risk of abnormal body temperature through the output interface in operation 750. In this case, the electronic device may generate a trend graph showing a rate of core body temperature change over a predetermined period of time, and may output the graph through the output interface. In this case, in order to provide a user with a warning, the electronic device may output a predetermined graphic object at a position corresponding to a time point, at which the rate of core body temperature change is greater than or equal to the threshold value, on the graph. Further, upon determining that the core body temperature is abnormal, the electronic device may also provide notification information requesting to stop outdoor activities by using a text message or a voice message.

In addition, the electronic device may directly estimate core body temperature by applying the estimated rate of core body temperature change to the core body temperature at the previous time, and if the estimated core body temperature falls outside a predetermined threshold range, the electronic device may provide the user with notification information about the risk of abnormal body temperature.

FIGS. 9 to 12 are diagrams illustrating examples of structures of an electronic device.

Figure 9:
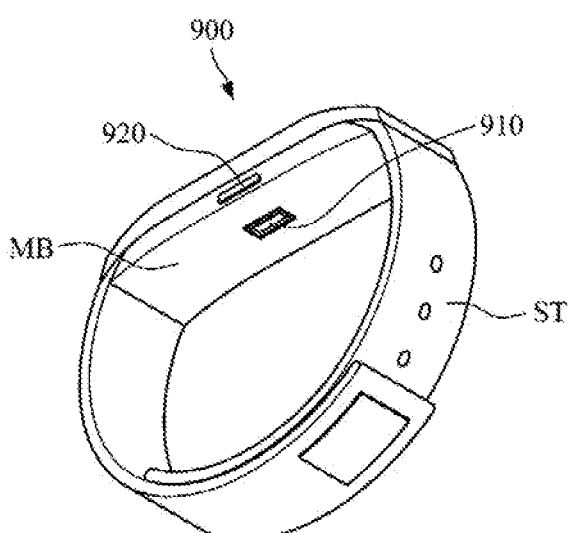
FIGS. 9 to 12 are diagrams illustrating examples of structures of an electronic device.

Referring to FIG. 9, the electronic device may be implemented as a smart watch wearable device 900 including a main body MB and a wrist strap ST.

The main body MB may be formed in various shapes. A battery may be embedded in the main body MB and/or the strap ST to supply power to various components of the wearable device. The strap ST may be connected to both ends of the main body to allow the main body to be worn on a user's wrist, and may be flexible so as to be wrapped around the user's wrist. The strap ST may be composed of a first strap and a second strap which are separated from each other. One end of each of the first strap and the second strap may be connected to both sides of the main body MB, and the first and second straps may be connected to each other via a fastening means formed at the other ends thereof. In this case, the fastening means may be formed as magnetic fastening, Velcro fastening, pin fastening, etc., but is not limited thereto. Further, the strap ST is not limited thereto, and may be integrally formed as a non-detachable band.

The main body MB may include a sensor 910, a processor, an output interface, a storage, and a communication interface. However, some of the output interface, storage, and the communication interface may be omitted depending on the size and shape of a form factor and the like.

The sensor 910 may include a first sensor for measuring a user's skin temperature, a second sensor for measuring heat flux vertically transmitted from skin to the main body, and a third sensor for measuring a user's heart rate. In this case, the sensor 910 may be disposed on a rear surface of the main body MB, so that when the main body MB is worn on the user's wrist, the sensor 910 may come into contact with an upper part of the user's wrist to estimate a rate of core body temperature change.

The processor mounted in the main body MB may be electrically connected to various components as well as the sensor 1010. The processor may estimate a rate of core body temperature change based on the skin temperature measured by the first sensor at a previous time, the heat flux measured by the second sensor at a previous time, the heart rate measured by the third sensor at a previous time, and skin temperature measured at a current time.

A display may be provided on a front surface of the main body MB and may display various application screens, including information on the rate of core body temperature change, time information, received message information, and the like. In addition, if the rate of core body temperature change is greater than or equal to a predetermined threshold value, the processor may provide a user with notification information about the risk of abnormal body temperature through a display. Information that may be displayed on the display is not limited thereto.

Figure 10:
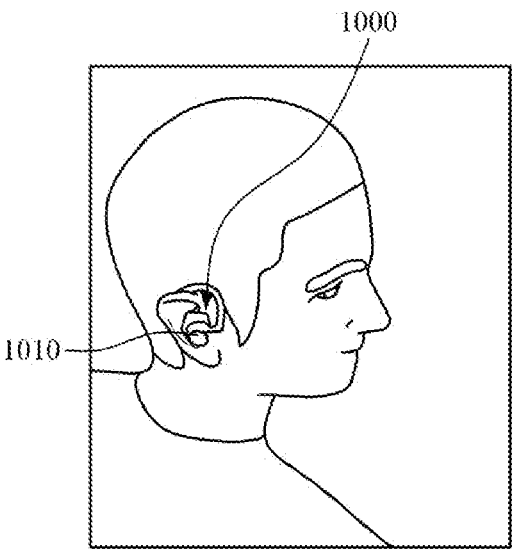

Referring to FIG. 10, the electronic device may be implemented as an ear-wearable device 1000.

The ear-wearable device 1000 may include a main body and an ear strap. A user may wear the ear-wearable device 1000 by hanging the ear strap on the user's auricle. The ear strap may be omitted depending on the shape of the ear-wearable device 1000. The main body may be inserted into the external auditory meatus. A sensor device 1010 may be mounted in the main body. The ear-wearable device 1000 may provide a user with an estimation result of a rate of core body temperature change or core body temperature estimated based on the rate of core body temperature change as sound, or may transmit the values to an external device, e.g., mobile device, tablet PC, etc., through a communication module provided in the main body.

Figure 11:
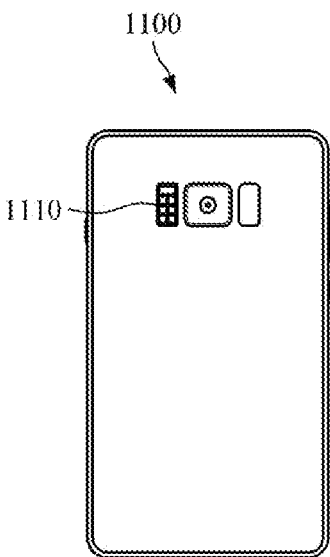

Referring to FIG. 11, the electronic device may be implemented as a mobile device 1100 such as a smartphone.

The mobile device 1100 may include a housing and a display panel. The housing may form an outer appearance of the mobile device 1100. The housing has a first surface, on which a display panel and a cover glass may be disposed sequentially, and the display panel may be exposed to the outside through the cover glass. A sensor 1110, a camera module and/or an infrared sensor, and the like may be disposed on a second surface of the housing.

For example, a plurality of temperature sensors for obtaining data from a user may be disposed on a rear surface of the mobile device 1100, and a fingerprint sensor disposed on the front surface of the mobile device 1100, a power button or a volume button disposed on a side surface thereof, sensors disposed at other positions of the front and rear surfaces of the mobile device 1100, and the like may be provided to estimate a rate of core body temperature change or to estimate core body temperature by using the estimated rate of change.

For example, when a user transmits a request for estimating a rate of core body temperature change by executing an application and the like installed in the mobile device 1100, the mobile device 1100 may obtain data by using the sensor 1110, and may estimate the rate of core body temperature change and provide the estimated value and/or notification information about the risk of abnormal body temperature to the user as image and/or sound by using the processor in the mobile device 1100.

Figure 12:
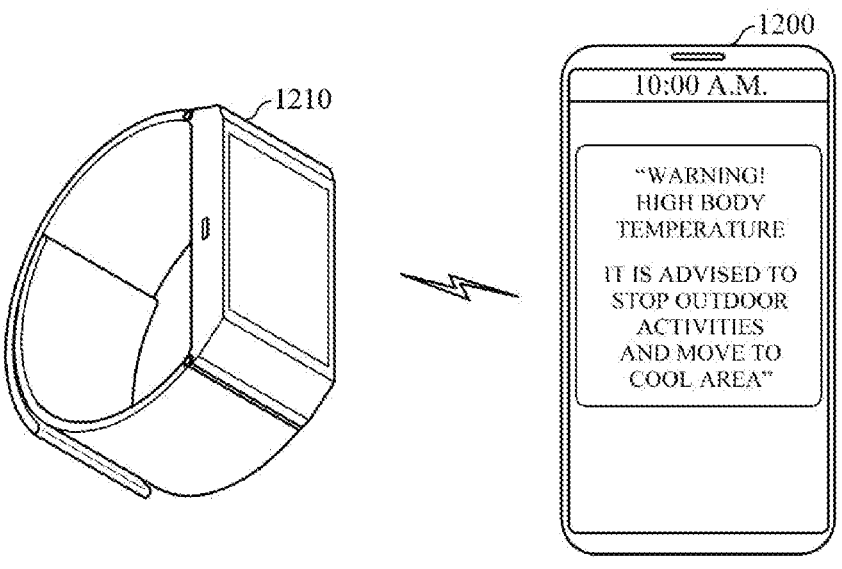

Referring to FIG. 12, the electronic device may be implemented as a combination of a wristwatch-type wearable device and a mobile device such as a smartphone. For example, a memory, a communication interface, and a processor for estimating a rate of core body temperature change may be mounted in a main body of a mobile device 1200. Upon receiving a request for estimating a rate of core body temperature change, the processor of the mobile device 1200 may control the communication interface to communicate with a communication module mounted in a main body of the wearable device 1210, to obtain data through the communication interface. Further, upon receiving data, such as skin surface temperature, heat flux, heart rate, and the like from the wearable device, the processor may estimate a rate of core body temperature change, and if the estimated rate of core body temperature change is greater than or equal to a predetermined threshold value, the processor may output notification information about the risk of abnormal body temperature to the display of the mobile device through an output interface as illustrated herein.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

What is claimed is:

1. An electronic device comprising:
a first sensor configured to measure a skin temperature of skin of a user;
a second sensor configured to measure heat flux transmitted from the skin to a main body of the electronic device;
a third sensor configured to measure a heart rate of the user; and
a processor configured to:
estimate a rate of skin temperature change based on the skin temperature measured at a first time and a second time;
estimate energy metabolism based on the heart rate measured by the third sensor and a maximum heart rate that corresponds to a user profile of the user; and
estimate a rate of core body temperature change based on the rate of the skin temperature measured at the first time and the second time, the heat flux, and the energy metabolism.

2. The electronic device of claim 1, wherein in response to the rate of core body temperature change being greater than or equal to a predetermined threshold value, the processor is further configured to provide notification information about risk of abnormal body temperature.

3. The electronic device of claim 2, wherein the processor is further configured to generate a trend graph showing the rate of core body temperature change over a predetermined period of time.

4. The electronic device of claim 3, wherein the processor is further configured to generate a graphic object at a position corresponding to a time point, at which the rate of core body temperature change is greater than or equal to the threshold value, on the trend graph to provide the user with a warning.

5. The electronic device of claim 2, wherein based on a core body temperature being determined to be abnormal, the processor is further configured to provide notification information requesting the user to stop an outdoor activity by using a text message or a voice message.

6. The electronic device of claim 1, wherein the first time precedes the second time, and wherein the processor is further configured to estimate a core body temperature at the second time by applying the rate of core body temperature change to the core body temperature measured at the first time.

7. The electronic device of claim 6, wherein in response to the estimated core body temperature falling outside a predetermined threshold range, the processor is further configured to provide notification information about a risk of abnormal body temperature.

8. The electronic device of claim 1, further comprising a temperature sensor spaced apart from the first sensor, and configured to measure an internal temperature inside the main body and measure the heat flux based on the skin temperature and the internal temperature inside the main body.

9. The electronic device of claim 8, wherein at least one of the first sensor and the temperature sensor is a thermistor.

10. The electronic device of claim 1, wherein a vertical distance between a contact surface of the main body and the first temperature sensor is 5 mm in a thickness direction of the main body.

11. The electronic device of claim 1, wherein the third sensor is at least one of a Photoplethysmography (PPG) sensor and an electrocardiography (ECG).

12. A method of estimating a rate of core body temperature change in an electronic device, the method comprising:
measuring a skin temperature of skin of a user;
measuring heat flux transmitted from the skin to a main body of the electronic device;
measuring a heart rate of the user;
estimate a rate of skin temperature change based on the skin temperature measured at a first time and a second time;
estimate energy metabolism based on the heart rate and a maximum heart rate that corresponds to a user profile of the user; and

estimate the rate of core body temperature change based on the rate of the skin temperature measured at the first time and the second time, the heat flux, and the energy metabolism.

13. The method of claim 12, further comprising, in response to the rate of core body temperature change being greater than or equal to a predetermined threshold value, providing the user with notification information about risk of abnormal body temperature through an output interface.

14. The method of claim 13, wherein the providing of the notification information about the risk of abnormal body temperature comprises generating a trend graph showing the rate of core body temperature change over a predetermined period of time.

15. The method of claim 12, wherein the first time precedes the second time, and
wherein the method further comprises: estimating a core body temperature by applying the rate of core body temperature change to the core body temperature measured at the first time.

16. A wearable device comprising:
a main body;
a strap connected the main body;
a skin temperature sensor configured to measure a skin temperature of a user at a first time and a second time;
a heat flux sensor configured to measure a heat flux between a skin of the user and the main body;
a heart rate sensor configured to measure a heart rate of the user; and
a processor configured to:
estimate a rate of skin temperature change based on the skin temperature measured at the first time and the second time;
estimate energy metabolism based on the heart rate and a maximum heart rate that corresponds to a user profile of the user; and
estimate a rate of core body temperature change based on the rate of the skin temperature measured at the first time and the second time, the heat flux, and the energy metabolism.

17. The wearable device of claim 16, further comprising a display,
wherein in response to the rate of core body temperature change being greater than or equal to a predetermined threshold value, the processor is further configured to provide notification information about a risk of abnormal body temperature through the display.

* * * * *